US010588615B2

(12) United States Patent
Baker

(10) Patent No.: US 10,588,615 B2
(45) Date of Patent: Mar. 17, 2020

(54) CONNECTED FASTENERS, DELIVERY DEVICE AND METHOD

(71) Applicant: EndoGastric Solutions, Inc., Redmond, WA (US)

(72) Inventor: Steve G. Baker, Redmond, WA (US)

(73) Assignee: EndoGastric Solutions, Inc., Redmond, WA (US)

( * ) Notice: Subject to any disclaimer, the term of this patent is extended or adjusted under 35 U.S.C. 154(b) by 287 days.

(21) Appl. No.: 15/729,630

(22) Filed: Oct. 10, 2017

(65) Prior Publication Data

US 2018/0028174 A1 Feb. 1, 2018

Related U.S. Application Data

(60) Division of application No. 15/239,527, filed on Aug. 17, 2016, now Pat. No. 9,788,829, which is a continuation of application No. 12/008,251, filed on Jan. 8, 2008, now Pat. No. 9,421,006.

(60) Provisional application No. 60/879,402, filed on Jan. 8, 2007.

(51) Int. Cl.

| | |
|---|---|
| ***A61B 17/04*** | (2006.01) |
| ***A61B 17/00*** | (2006.01) |
| *A61B 17/11* | (2006.01) |

(52) U.S. Cl.

CPC .... *A61B 17/0401* (2013.01); *A61B 17/00234* (2013.01); *A61B 17/0487* (2013.01); *A61B 17/1114* (2013.01); *A61B 2017/0409* (2013.01); *A61B 2017/0417* (2013.01); *A61B 2017/0464* (2013.01); *A61B 2017/1142* (2013.01)

(58) Field of Classification Search

CPC .... A61F 5/0063; A61F 5/0033; A61F 5/0086; A61F 5/0003; A61B 2017/0462; A61B 17/0401; A61B 2017/0409; A61B 17/0487; A61B 2017/1142; A61B 2017/0464

See application file for complete search history.

(56) References Cited

U.S. PATENT DOCUMENTS

2006/0151568 A1* 7/2006 Weller ............... A61B 17/0218 227/175.1
2007/0276409 A1* 11/2007 Ortiz .................. A61B 17/0682 606/139

* cited by examiner

*Primary Examiner* — Shaun L David
*Assistant Examiner* — Christina C Lauer
(74) *Attorney, Agent, or Firm* — Fulwider Patton LLP

(57) ABSTRACT

A device for reducing the volume of a hollow body organ includes a tissue port and a plurality of fasteners. The fasteners may be coupled to a flexible filament, such as a suture, which is tensioned to constrict the hollow body organ to achieve volume reduction.

3 Claims, 10 Drawing Sheets

417
411
400
411
410
410
419
418
424
413
408
402

CONNECTED FASTENERS, DELIVERY DEVICE AND METHOD

This Preliminary Amendment is being filed concurrently with an application that is a division of U.S. Ser. No. 15/239,527 filed Aug. 17, 2016, which is a division of U.S. Ser. No. 12/008,251 filed Jan. 8, 2008, which issued as U.S. Pat. No. 9,421,006, which is a division of U.S. Ser. No. 60/879,402 filed Jan. 8, 2007, the entirety of each of which are incorporated herein by reference.

BACKGROUND OF THE INVENTION

The present invention is directed to methods and devices for applying fasteners to the stomach or esophagus. The present invention is also directed to methods and devices for restricting the esophagus and/or stomach.

SUMMARY

The delivery device carries fasteners connected to suture. A suture holder such as a sliding knot or adjustable clamp or a crimp sleeve can adjust the length of the connected suture smaller or larger. In the preferred embodiment the suture holder is pre-attached to the suture. For example the suture holder can connect the ends of the suture to form a loop. The delivery device is introduced through the mouth and esophagus into the stomach. The delivery device fastens the tissue with the fasteners.

An adjusting device pulls the suture, which in turn pull the fasteners and the fastened stomach tissue. This reduces the internal size of the stomach and creates a restrictive gastric pouch.

The delivery device has a tissue chamber and one or more tissue ports. The tissue chamber can be radially collapsed for introduction into and removal from the patient. After entering the stomach, the tissue chamber can be radially expanded. This reduces folding of the stomach during tissue retraction and enables more accurate placement of fasteners. Tissue is retracted through the tissue port into the tissue chamber and then fastened. For example the tissue can be retracted by suction or mechanical grasping.

The suture and fasteners can be pre-loaded on and in the delivery device such that after fastening the fasteners and suture are completely releasable from the delivery device without the need to separate the parts of the device.

The suture can wrap around the outside of the tissue chamber as it passes from one tissue port to the next. The suture can be partially or completely covered for easier introduction of the device into the patient. For example the suture loop can be placed in a recessed groove. The suture can be at least partially covered by a membrane with a releasable adhesive bond to the device, a tearable membrane, a flap with a free edge, or by a removable sheath.

The fasteners and suture can be delivered in a position and sequence such that the suture forms one of several desired shapes such as an approximately circular loop or a zigzag or a figure eight or overlapping diametral segments. These shapes affect the shape of the tissue.

DESCRIPTION OF THE PREFERRED EMBODIMENTS

Figure 1:
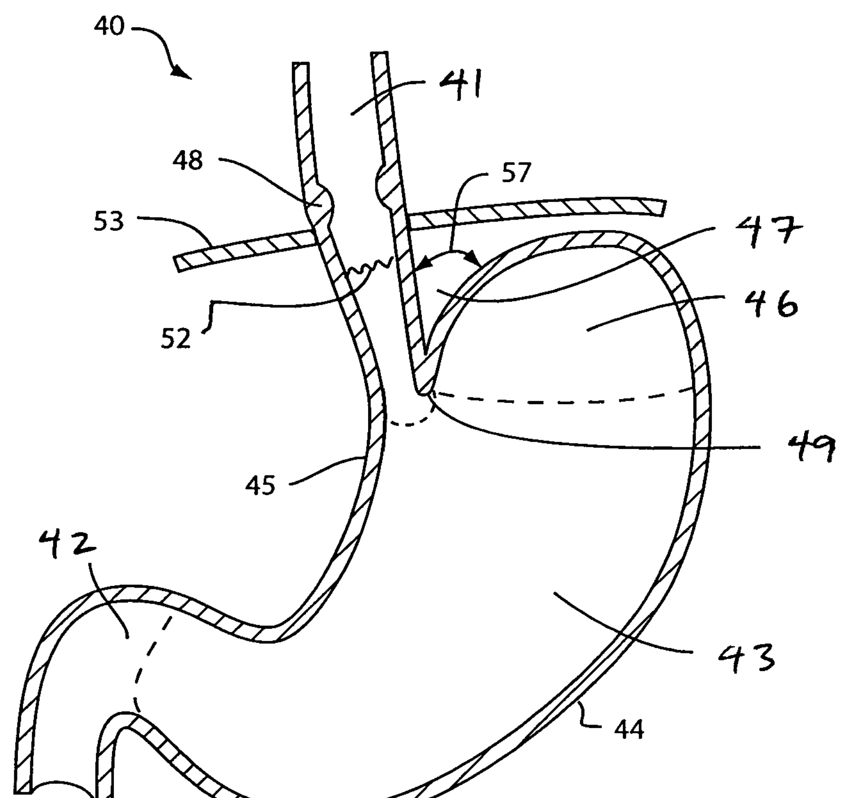
FIG. 1 shows a stomach.

Referring to FIG. 1, a gastroesophageal region 40 is shown which includes an esophagus 41 leading to a stomach 43. The stomach 43 includes a greater curvature 44 and a lesser curvature 45 and a fundus 46. A cardiac notch 47 is formed at the junction between the esophagus 41 and the stomach 43 which forms an angle of HIS 57. A gastroesophageal junction 52 lies between a lower esophageal sphincter 48 and a gastroesophageal flap valve 49. A diaphragm 53 extends around the stomach 43.

Figure 2:
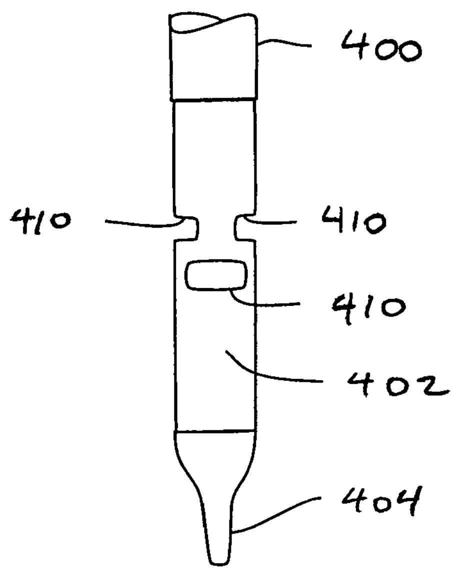
FIG. 2 shows a fastener delivery device having a tissue chamber and tissue ports.
Figure 3:
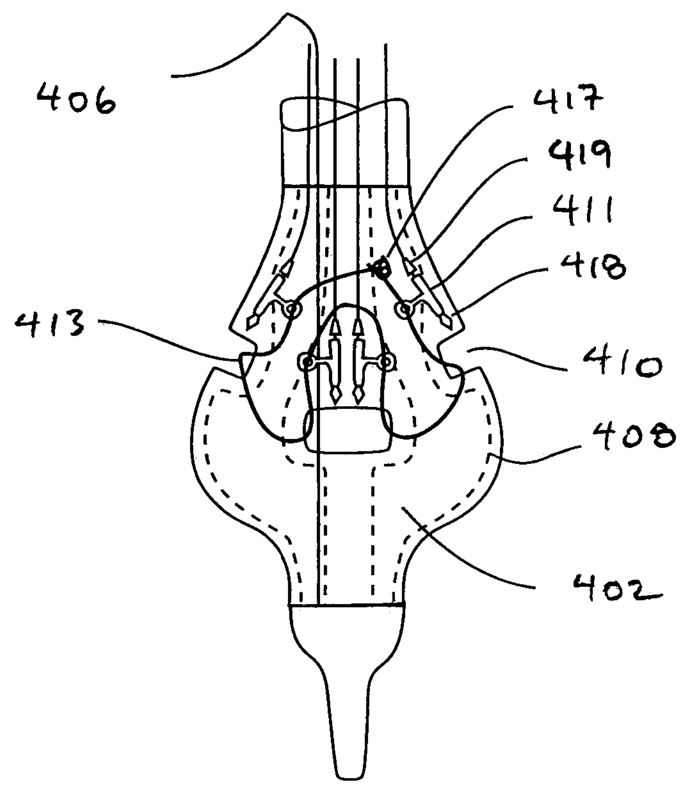
FIG. 3 shows a radially expandable tissue chamber.
Figure 4:
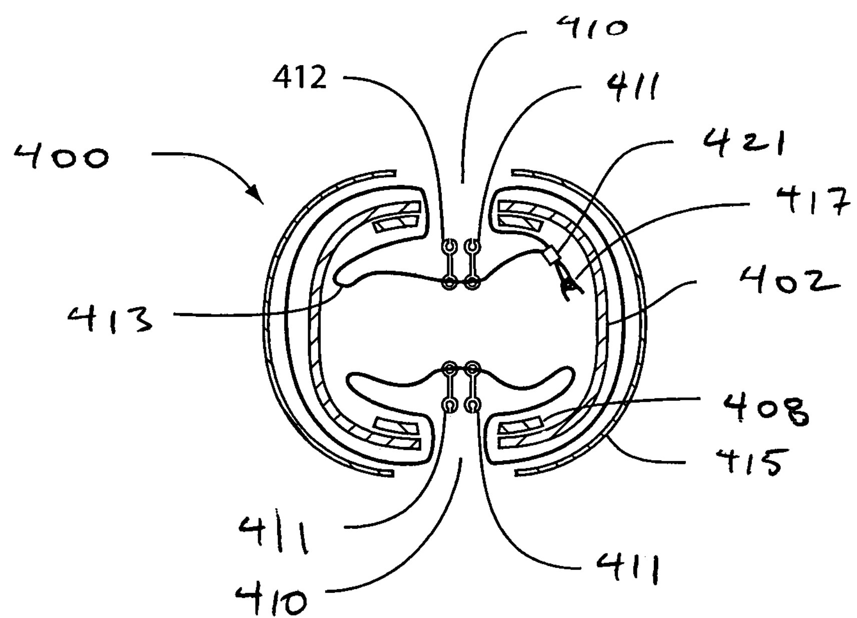
FIG. 4 shows a cross section of the delivery device with fasteners connected by a suture loop.

Referring to FIGS. 2-4, a delivery device 400 is shown which has a tissue chamber 402 and one or more tissue ports 410. Tissue is drawn into the tissue ports 410 and fastened together with fasteners 411. Tissue is drawn into the tissue ports 410 using suction although a mechanical grasper may also be used. The device 400 may include a valve 404, such as a duck bill valve, at the distal end which may receive an endoscope as is known in the art.

Referring to FIG. 3 and FIG. 4, the tissue chamber 402 may be expanded by tensioning a control line 406 which causes the tissue chamber 402 to expand and bow outward. Expansion of the tissue chamber 402 may help to prevent excessive folding of the tissue while permitting a relatively large amount of tissue to create the tissue fold. The device 400 includes struts 408 which support the tissue chamber 402 and help to form a desired shape when the tissue chamber 402 is expanded.

The device 400 is loaded with a number of fasteners 411 and a flexible filament 413 such as suture 415 or the like. The filament 413 may form a closed loop with a knot 417 or other suitable method of securing one part of the filament 413 to another to maintain tension on the filament 413 as described below. The filament 413 may extend out of one of the tissue ports 410 and re-enter the device through another tissue port 410 as shown in FIG. 3. The filament 413 may be covered by a flap 415 which covers the filament 413 while permitting release of the filament 413 through a free edge.

Figure 5:
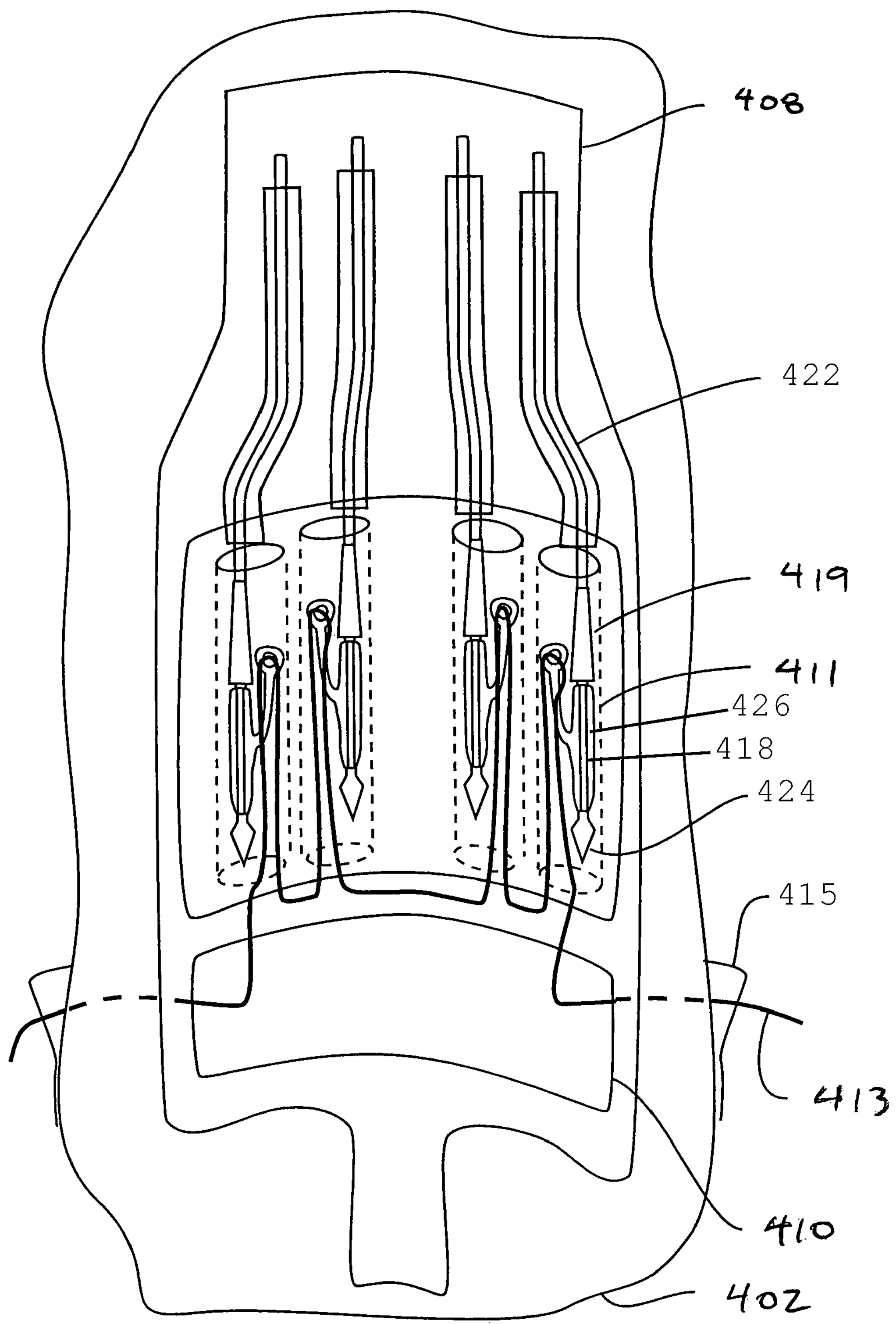
FIG. 5 shows a cutaway portion of the device viewed from inside the tissue chamber.

Referring to FIG. 5, the fasteners and filament 413 are shown positioned above the tissue port. The fasteners 411 are mounted to a stylet 418 having a pusher 419 that is positioned in a stylet tube 422. The stylet 418 has a sharp tip 424 which is used to penetrate tissue. The fastener 411 may have a groove 426 or other feature which permits release of the fastener 411 from the stylet 418. A number of fasteners 411 may be deployed through each of the tissue ports 410 as explained below. The flap 415 covers the portion of the filament 413 extending from one of the tissue ports to an adjacent tissue port 410.

Figure 6:
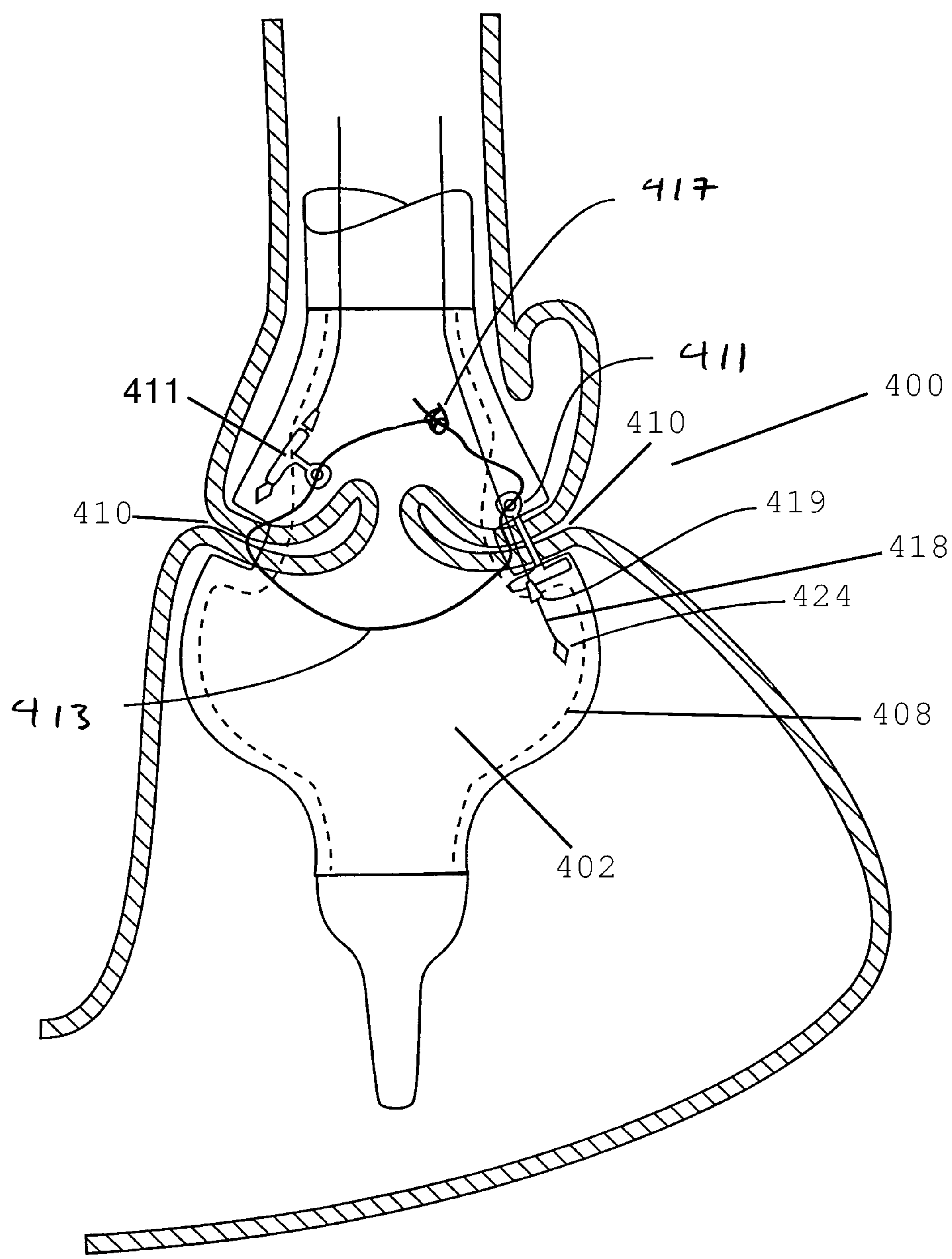
FIG. 6 shows the fastener delivery device in the stomach. The tissue chamber is radially expanded. Tissue is retracted into the tissue chamber through the tissue ports.
Figure 7:
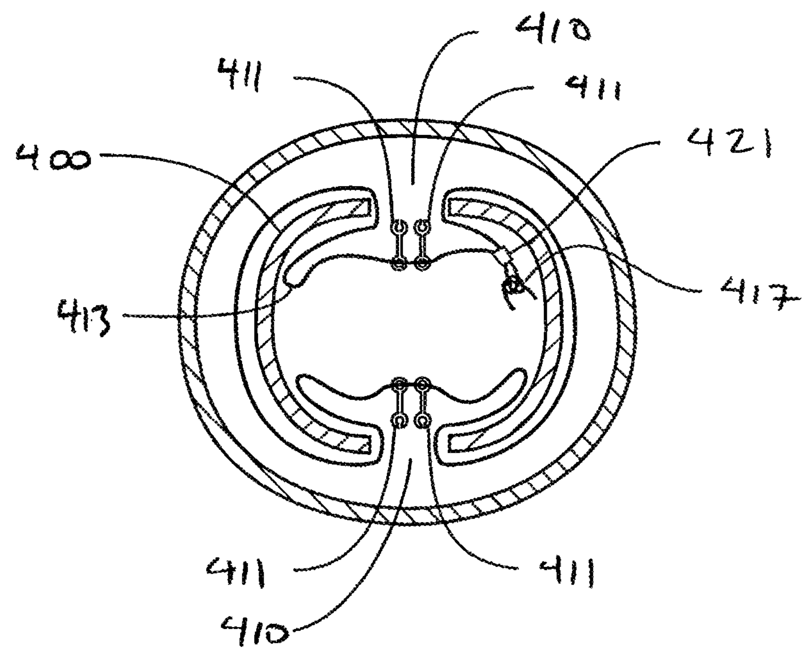
FIG. 7 shows a cross sectional view of the fastener delivery device in the stomach.
Figure 8:
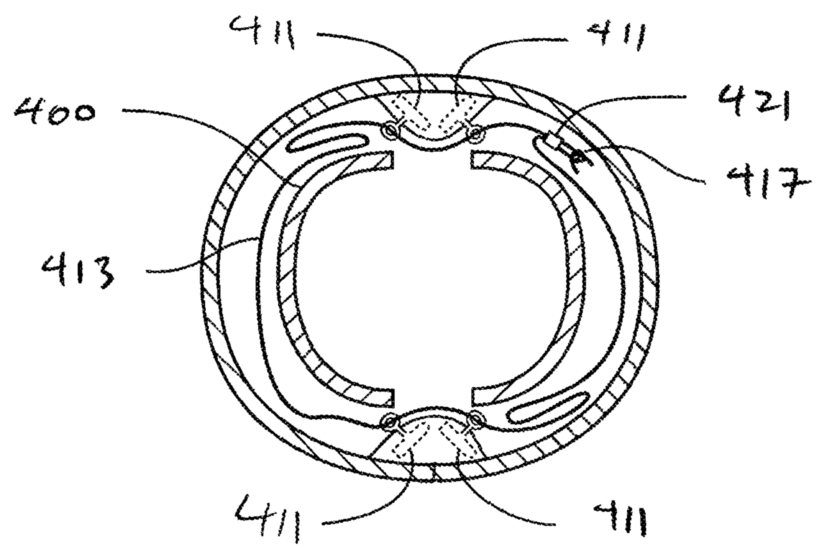
FIG. 8 shows fasteners deployed in a sequence to place a suture loop in an approximately circumferential orientation.
Figure 9:
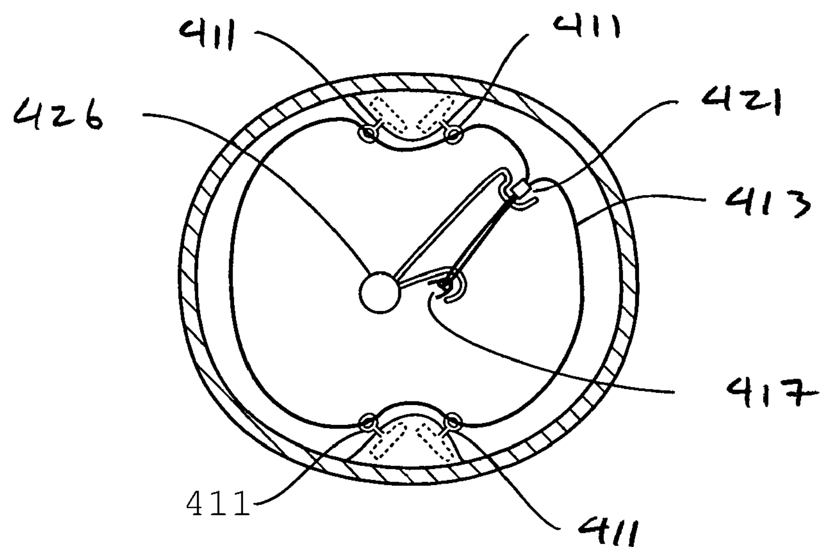
FIG. 9 shows the adjusting device sliding the suture holder to reduce the length of the suture loop.
Figure 10:
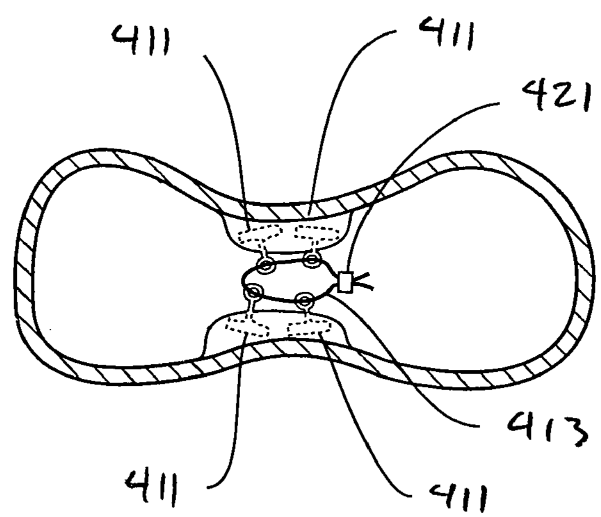
FIG. 10 shows the suture tightened to reduce the luminal area of the stomach.

Referring now to FIG. 6, the device 400 is shown with the tissue chamber 402 expanded. Tissue is drawn into the tissue ports 410 to form a tissue fold in each of the tissue ports 410. The fasteners 411 are then driven through the tissue folds using the stylet 418. The filament 413 may then be tensioned to draw the fasteners 411 together. In this manner, a hollow body structure such as the stomach may be reduced in volume. FIGS. 7 and 8 show two fasteners 411 deployed from each tissue port 410. Referring to FIG. 9, the filament 413 may be tensioned to draw the tissue structures together as shown in FIG. 10 to form two lobes in the stomach. Tension on the filament 413 may be applied and maintained using a tightening device 426 which may create a knot or use a sleeve 421 to tighten and maintain tension on the filament 413.

Figure 11:
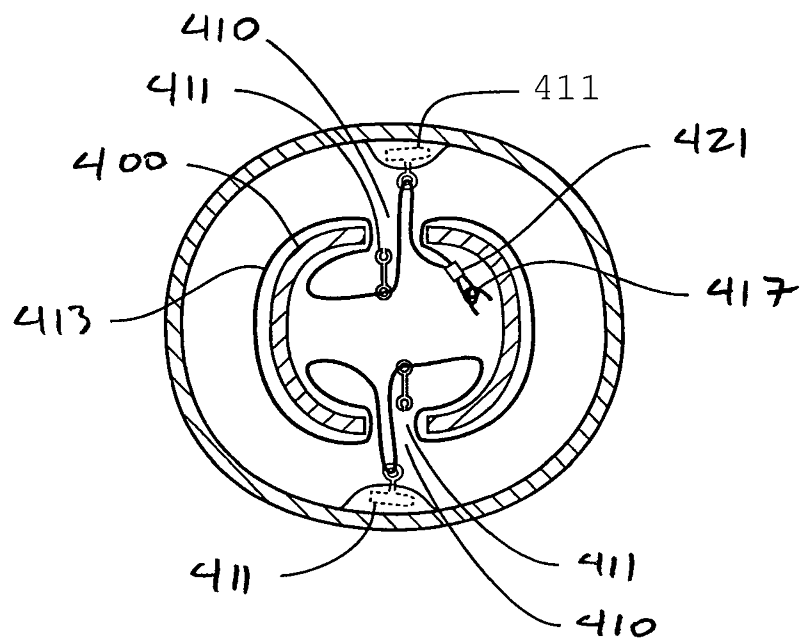
FIG. 11 shows two fasteners deployed from two tissue ports approximately 180 degrees apart.
Figure 12:
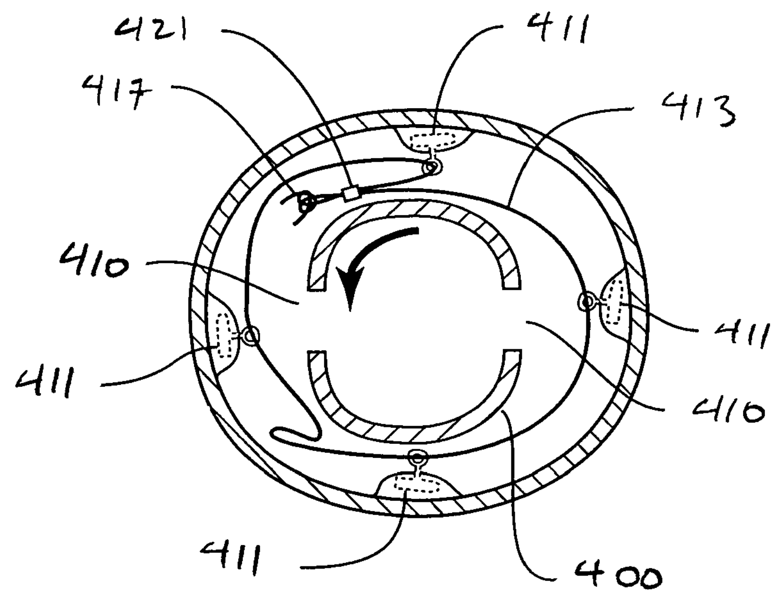
FIG. 12 shows rotating the device approximately 90 degrees and deploying two more fasteners approximately midway between the first two fasteners.
Figure 13:
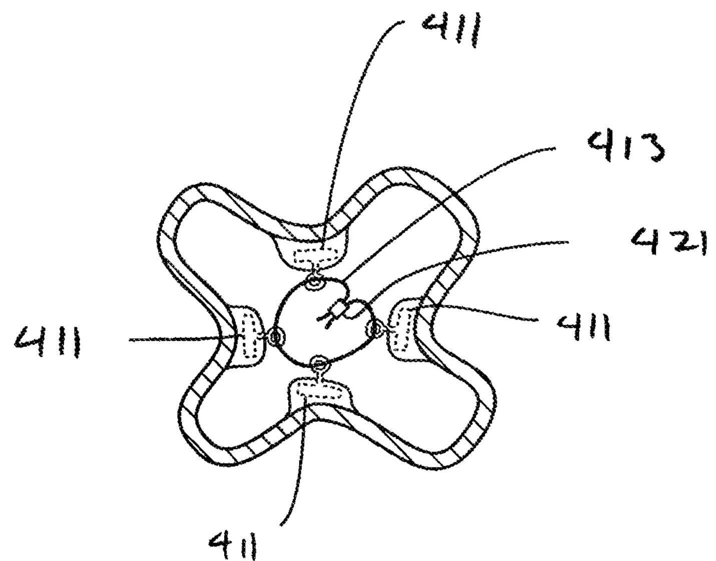
FIG. 13 shows the suture tightened to reduce the luminal area of the stomach.
Figure 14:
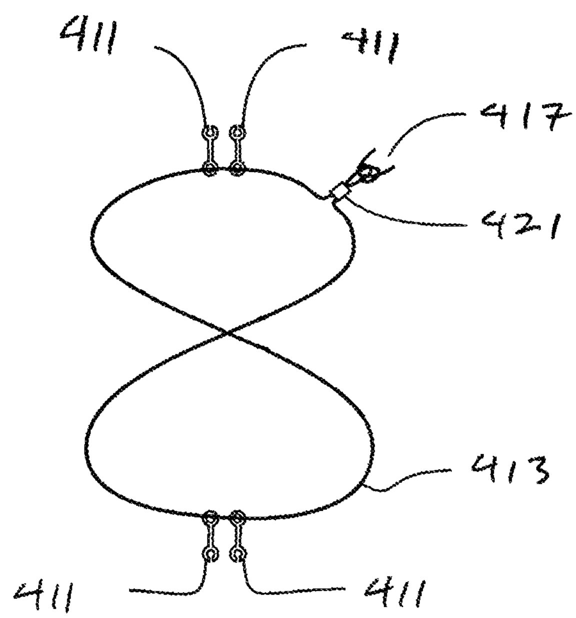
FIG. 14 shows the suture before loading into the device in which the suture loop crosses itself to form a "figure 8" shape.
Figure 15:
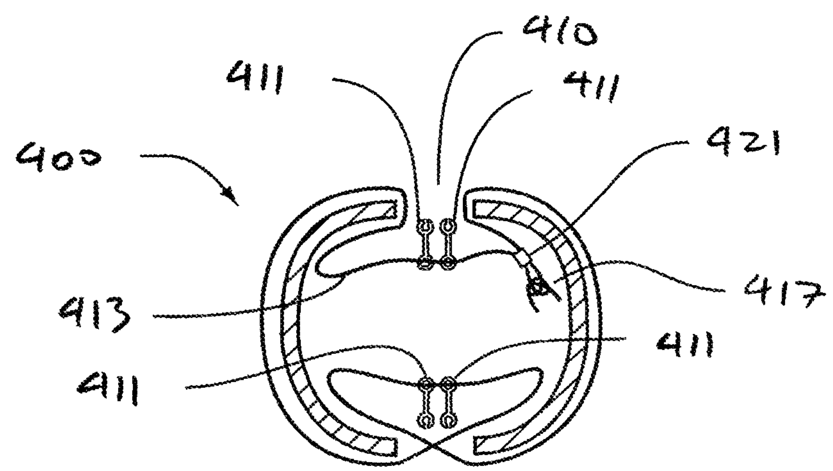
FIG. 15 shows the crossed suture and fasteners loaded into the delivery device.
Figure 16:
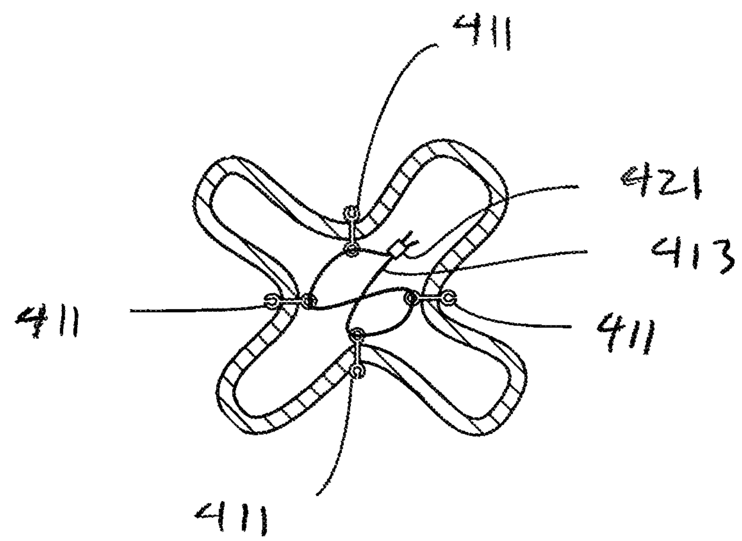
FIG. 16 shows the "figure 8" loop in the stomach, with the suture oriented partly circumferential and partly diametral. In this example each fastener penetrates a single layer of tissue.

Referring now to FIGS. 11-13, still another method of using the device 400 is shown. One fastener 411 is delivered through each of the tissue ports 410 as shown in FIG. 11. The device 400 is then rotated to the position of FIG. 12 and two more fasteners 411 are deployed. The filament 413 may then be tensioned to form four lobes in the stomach. Referring to FIGS. 14-16, the filament 413 may also be configured to extend across the hollow body structure in a pattern similar to a figure-8. FIG. 15 shows the filament 413 loaded onto the delivery device 400. Two of the fasteners 411 are deployed through the tissue ports 410 and the device 400 is rotated and two more fasteners 411 are deployed. The filament 413 is then tensioned to draw the tissue structure together as shown in FIG. 16.

Figure 17:
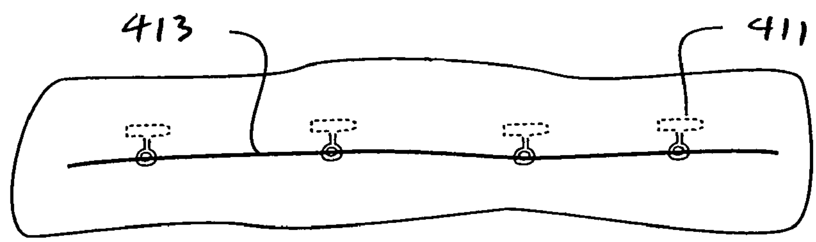
FIG. 17 shows an intraluminal view of fasteners deployed into tissue.
Figure 18:
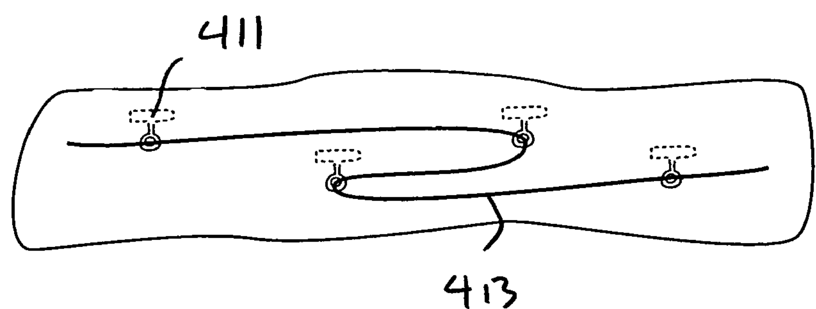
FIG. 18 shows fasteners deployed to place the suture in a "backstitched" orientation.
Figure 19:
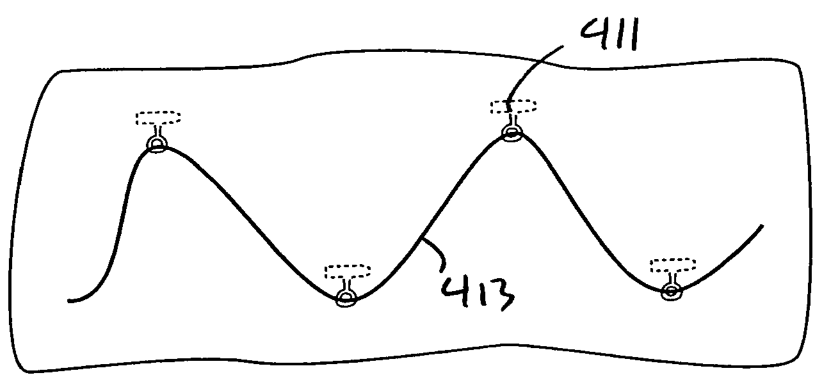
FIG. 19 shows fasteners deployed at varying axial heights to place the suture in a zigzag orientation.

FIGS. 17-19 show various configurations for the filament 413. FIG. 17 shows the filament 413 deployed in an approximately planar ring. FIG. 18 shows the filament 413 in a backstitched orientation. FIG. 18 shows fasteners can be deployed to place the suture in a “backstitched” orientation. For example, the device can be rotated between sequential fastener deployments. As may be appreciated from the figure, when the suture is tightened further the fasteners will pull tissue sideways.

FIG. 19 shows the filament 413 in a zigzag orientation at varying axial heights. A zigzag loop can increase the number of tissue folds such that the outlet area from a gastric pouch is reduced more than from a non zigzag loop. As may be appreciated from FIG. 19, when the suture is tightened further the zigzag will decrease in axial amplitude and the fasteners will pull tissue axially closer together as well as circumferentially closer together.

Placing the fasteners in the desired pattern alters the shape of the suture loop. In turn this alters the suture’s direction of pull on the fasteners and the fasteners direction of pull on the tissue. This can be used to cause the tissue to fold in beneficial ways.

Fastening a single suture such that multiple segments have tension components in the same direction increases the force on the tissue in that direction. For example a diametrically oriented suture can be more efficient at pulling tissue radially inward than a circumferential suture.

The tensioning element or suture holder may be a sliding knot such as a Roeder knot. The tensioning element or not may also be a clip that is crimped to the suture loop or a sleeve that can slide on the suture loop. The adjusting device can also be a flexible endoluminal crimper that crimps the suture holder to hold the suture.

The present invention has been described with reference to preferred embodiments; however, numerous changes may be made without departing from the scope of the invention.

The invention claimed is:

1. An assembly for forming a fold of tissue, comprising:

a device having a body and a tissue chamber coupled to the body, the tissue chamber being expandable, the device also having a plurality of tissue ports configured to draw a fold of tissue into each of the tissue ports using suction, the tissue ports being positioned along the tissue chamber so that the fold of tissue extends into the tissue chamber, the device also having a plurality of fasteners and a flexible filament carried by the body, wherein each fastener is slidably mounted on a stylet and configured to be delivered through the fold of tissue extending into the tissue port and held in the tissue port using suction, the flexible filament being coupled to each of the plurality of fasteners and extending through one of the tissue ports and entering another of the tissue ports prior to deployment, and a tensioning device implanted inside the body to apply tension on the flexible filament and thereby pull on the fasteners and moving the first and second folds of tissue towards one another and securing the flexible filament with a knot inside the body.

2. The assembly of claim 1, wherein a pusher assembly advances the fasteners over the stylets and into the fold of tissue.

3. The assembly of claim 2, wherein a plurality of flexible struts support the tissue chamber and allow the tissue chamber to expand when the fold of tissue is drawn into the tissue chamber.

* * * * *